(12) United States Patent
Turner et al.

(10) Patent No.: US 8,834,478 B2
(45) Date of Patent: Sep. 16, 2014

(54) MEDICAL DEVICE AND METHOD

(75) Inventors: Nicholas Robert Turner, Cheltenham (GB); Matthew Cannell, Rugby (GB)

(73) Assignee: T. J. Smith & Nephew Limited, Hull (GB)

( * ) Notice: Subject to any disclaimer, the term of this patent is extended or adjusted under 35 U.S.C. 154(b) by 373 days.

(21) Appl. No.: 12/866,590

(22) PCT Filed: Feb. 9, 2009

(86) PCT No.: PCT/GB2009/000362
§ 371 (c)(1),
(2), (4) Date: Nov. 9, 2010

(87) PCT Pub. No.: WO2009/098491
PCT Pub. Date: Aug. 13, 2009

(65) Prior Publication Data
US 2011/0060342 A1    Mar. 10, 2011

(30) Foreign Application Priority Data
Feb. 7, 2008    (GB) .................................. 0802277.4

(51) Int. Cl.
*A61B 17/58*    (2006.01)
*A61F 2/46*    (2006.01)
*A61F 2/34*    (2006.01)
*A61F 2/30*    (2006.01)

(52) U.S. Cl.
CPC ....... *A61F 2/4609* (2013.01); *A61F 2002/4627* (2013.01); *A61F 2/34* (2013.01); *A61F 2002/3054* (2013.01); *A61F 2002/4681* (2013.01)
USPC .......................................................... 606/91

(58) Field of Classification Search
CPC .................................. A61F 2/4609; A61F 2/34
USPC .......................................................... 606/91
See application file for complete search history.

(56) References Cited

U.S. PATENT DOCUMENTS 4,023,572 A    5/1977    Weigand et al.
4,662,891 A *  5/1987    Noiles ........................ 623/22.31

(Continued)

FOREIGN PATENT DOCUMENTS

AU    2001262308    12/2001
DE    10 2006 043 783    3/2008

(Continued)

OTHER PUBLICATIONS

Search Report; Chinese Patent Office; Chinese Patent Application 200980104466.3; Jan. 21, 2013, 4 pages.

(Continued)

*Primary Examiner* — Nicholas Woodall
(74) *Attorney, Agent, or Firm* — Krieg DeVault LLP

(57) ABSTRACT

A device (1) for connecting to an implant (16), comprising: at least two protrusions (8, 9) connectable, in use, to at least one indentation (20) in the implant; and a mechanism for moving the protrusions between a connected and a disconnected position. An implant (16) comprising a body (17) having at least one indentation (20) disposed within the body, wherein, in use, the at least one indentation receives at least two protrusions (8, 9) of a device (1) for connecting to the implant (16) such that the implant is clamped by the device. A method of connecting an implant (16) to a device (1).

20 Claims, 8 Drawing Sheets

(56) References Cited

U.S. PATENT DOCUMENTS

| | | | |
|---|---|---|---|
| 4,677,972 A * | 7/1987 | Tornier | 606/53 |
| 5,108,448 A | 4/1992 | Gautier | |
| 5,540,697 A * | 7/1996 | Rehmann et al. | 606/91 |
| 5,904,688 A * | 5/1999 | Gilbert et al. | 606/86 R |
| 5,928,287 A | 7/1999 | Keller | |
| 6,063,124 A * | 5/2000 | Amstutz | 623/22.21 |
| 7,727,282 B2 * | 6/2010 | Slone et al. | 623/22.12 |
| 2004/0186586 A1 * | 9/2004 | Seyer et al. | 623/22.12 |
| 2012/0023733 A1 * | 2/2012 | Cannell et al. | 29/525.01 |

FOREIGN PATENT DOCUMENTS

| | | |
|---|---|---|
| EP | 0453694 A1 | 10/1991 |
| FR | 2 721 502 | 12/1995 |
| FR | 2 830 746 | 4/2003 |
| FR | 2830746 A | 4/2003 |
| GB | 2445087 | 6/2008 |
| JP | H02-286159 | 11/1990 |
| JP | 2003-534096 | 11/2003 |

OTHER PUBLICATIONS

First Office Action; Chinese Patent Office; Chinese Patent Application 200980104466.3; Jan. 30, 2013, 11 pages.

Japanese Office Action; Japanese Patent Office; Japanese Patent Application No. 2010-545557; Sep. 10, 2013, 8 pages.

European Office Action; European Patent Office; European Patent Application No. 09708552.6; Apr. 28, 2014, 3 pages.

* cited by examiner

MEDICAL DEVICE AND METHOD

This application is a United States National Phase filing of International Application No. PCT/GB2009/000362 filed on Sep. 2, 2009 which claims priority to GB Patent Application No. 0802277.4 filed on Feb. 7, 2008, the disclosure of each prior document is incorporated herein by reference in its entirety.

The present invention relates to a device for connecting to and inserting an implant. The present invention also relates to an implant for connecting to such a device. The present invention also relates to methods using such devices and implants.

In hip resurfacing using a metal on metal bearing, it is essential that the acetabular component of the implant is securely attached to the introducer, which is a device used to insert and manipulate the acetabular component. The introducer needs to be secure enough to allow the implant to be fully inserted into the prepared acetabulum. The introducer also needs to be able to rotate and reposition the implant as required once it is inserted. The introducer also needs to be able to re-attach to the implant to allow it to be removed if it is determined it is incorrectly positioned.

For an acetabular implant which utilises a liner (for example polyethylene) this is relatively simple as an attachment can be made to the inside of the metal acetabular component which is then covered by the liner. However, for a metal on metal component which does not use a liner, attachment to the inside of the implant is not possible because it will compromise the bearing surface.

A known type of introducer connects to the acetabular implant by means of wires attached to the implant. Once the implant is in place, the wires are cut in order to remove the introducer. However, it is very difficult to reposition the implant after the wires have been cut.

Other known devices attach to features machined on the inside of the acetabular implant. However, creating features on the inside of the bearing surface can affect the performance of the implant. For example, the highly polished metal surface may be damaged. In addition, such features reduce the surface area of the prosthetic articulation. Furthermore, known devices which connect to the inside of the implant do not allow for a modular connection to account for all implant sizes.

Other known devices attach to the outside of the implant. However, in order to do this, when attaching the instrument it needs to exceed the outside diameter of the implant. However, in order to remove the instrument from the implant after it has been implanted, it is necessary for the instrument to be retracted to a size larger than the prepared acetabulum. This can cause the instrument to become trapped between the implant and the prepared bone.

It is an aim of the present invention to provide an implant and a device which have features such that the implant can be securely connected to the device, without compromising the articulating properties or structural strength of the implant. The implant can be easily connected to the instrument, both prior to implantation and after implantation (to allow the implant to be removed or repositioned).

According to a first aspect of the present invention, there is provided a device for connecting to an implant, comprising:
  at least two protrusions connectable, in use, to at least one indentation in the implant; and
  a mechanism for moving the protrusions between a connected and a disconnected position.

According to a second aspect of the present invention, there is provided a device for connecting to an implant, comprising:
  at least two protrusions connectable, in use, to at least one indentation in the implant;
  a mechanism for moving the protrusions between a connected and a disconnected position,
  wherein, in use, the protrusions connect to the at least one indentation such that the implant is clamped by the device.

According to a third aspect of the present invention, there is provided a device for connecting to an implant, comprising:
  at least two protrusions connectable, in use, to at least one indentation in the implant body, the implant body having an inner and an outer surface;
  a mechanism for moving the protrusions between a connected and a disconnected position,
  wherein, in use, the protrusions connect to the at least one indentation such that the protrusions do not protrude beyond the inner and/or outer surfaces of the implant body.

In the present application an indentation may be any means for receiving/accommodating a protrusion. For example, an indentation may be a recess or a groove.

In the present application a protrusion may be any means for connecting to, or being received/accommodated by, an indentation. For example, a protrusion may be a catch, peg or lug.

The protrusions may be chamfered. The protrusions may be in the form of a tapered catch. The protrusions may be in the form of a dovetail.

According to preferred embodiments of the present invention, the mechanism moves the protrusions independently of each other.

The mechanism may move the protrusions in different directions.

The mechanism may move the protrusions in opposite directions.

The mechanism may rotate the protrusions in different directions.

The mechanism may rotate the protrusions in opposite directions.

According to a fourth aspect of the present invention, there is provided a device for connecting to an implant, comprising:
  at least two protrusions connectable, in use, to at least one indentation in the implant; and
  a mechanism for moving the protrusions between a connected and a disconnected position,
  wherein the mechanism moves the protrusions independently of each other.

The mechanism may move the protrusions in different directions.

The mechanism may move the protrusions in opposite directions.

The mechanism may rotate the protrusions in different directions.

The mechanism may rotate the protrusions in opposite directions.

The device may be made of metal. The device may be made of stainless steel.

The device may be made of plastics. The device may be made of high density polyethylene. The device may be made of polyacetal. The device may be made of polyaryletheretherketone (PEEK).

The device may be made of a combination of metal and plastics.

According to a fifth aspect of the present invention, there is provided an implant comprising a body having at least one indentation disposed within the body, wherein, in use, the at least one indentation receives at least two protrusions of a device for connecting to the implant such that the implant is clamped by the device.

According to a sixth aspect of the present invention, there is provided an implant comprising:
 a body having an inner and an outer surface; and
 at least one indentation disposed within the body,
wherein, in use, the at least one indentation receives at least two protrusions of a device for connecting to the implant such that the protrusions do not protrude beyond the inner and/or outer surfaces of the implant body.

The implant may be an acetabular component. The implant may be an acetabular cup. The implant may be a resurfacing cup.

The acetabular cup may have an outside diameter in the range 44 to 68 mm. The acetabular cup may have an inside diameter in the range 38 to 62 mm.

The at least one indentation may be in the form of a bayonet connector.

The at least one indentation may be shaped so as to receive at least one chamfered protrusion. The at least one indentation may be shaped so as to receive at least one tapered catch. The at least one indentation may be shaped so as to receive at least one dovetail shaped protrusion.

The implant may be made of metal. The implant may be made of a metal alloy. The implant may be made of stainless steel. The implant may be made of titanium. The implant may be made of cobalt chrome.

According to a seventh aspect of the present invention, there is provided a method of connecting an implant to a device, comprising:
 providing a device for connecting to an implant, comprising at least two protrusions connectable, in use, to at least one indentation in the implant, and a mechanism for moving the protrusions between a connected and a disconnected position;
 providing an implant comprising at least one indentation; and
 connecting the device to the implant by operating the mechanism so as to move the protrusions from a disconnected to a connected position.

The protrusions may connect to the at least one indentation such that the implant is clamped by the device.

According to some embodiments of the present invention, the implant has an inner and an outer surface and the protrusions connect to the at least one indentation such that the protrusions do not protrude beyond the inner and/or outer surfaces of the implant body.

Methods according to the present invention may use any of the devices according to the first to fourth aspects of the present invention and/or any of the implants according to the fifth or sixth aspects of the present invention.

Advantages of the present invention include the following. According to some embodiments of the present invention, in use, the protrusions of the device connect to the at least one indentation such that the implant is clamped by the device. The connection between the implant and the device is therefore secure and stable which is clearly beneficial during insertion and manipulation of the implant.

According to some embodiments of the present invention, the device protrusions do not protrude beyond the inner surface of the implant body. Consequently, no modification of the inner bearing surface of the implant body is required.

According to some embodiments of the present invention, the device protrusions do not protrude beyond the outer surface of the implant body. Consequently, the device is more streamlined/compact, and less tissue damage occurs during use, making it suitable for use in minimally invasive surgery. The device can be easily re-connected after implantation of the acetabular component, enabling removal or repositioning of the implant.

The design of the device means that it is possible to have a series of modular connections to account for all implant sizes. This significantly reduces the total bulk of the instrument kit.

According to some embodiments of the present invention, no indentation(s) are provided on the inside bearing surface of the implant and consequently there is no effect on the performance of the implant.

According to some embodiments of the present invention, there is provided an acetabular implant component comprising a series of indentations disposed in multiple positions on the outer surface of the implant. The indentations are disposed on the outer domed face of the implant and are cut out to a depth midway through the thickness of the implant. The indentations are machined to the top flat face of the implant to allow the device to connect, and subsequently be removed, without the need to exceed the outside diameter of the implant.

According to some embodiments of the present invention, the at least two protrusions are in the form of tapered catches or dovetails.

According to some embodiments of the present invention, the at least one indentation disposed within the implant body has a tapered catch or dovetail design at either end. The associated device has two plates, each plate having a protrusion in the form of a tapered catch or dovetail. The dovetails on the two plates are identical in shape, but facing in opposite directions. By rotating the two plates relative to each other, the taper of each dovetail results in them 'clamping' the implant to the device rather than just attaching the implant to the device. This provides a much more secure and stable connection.

Reference will now be made, by way of example, to the accompanying drawings, in which.

Figure 1:
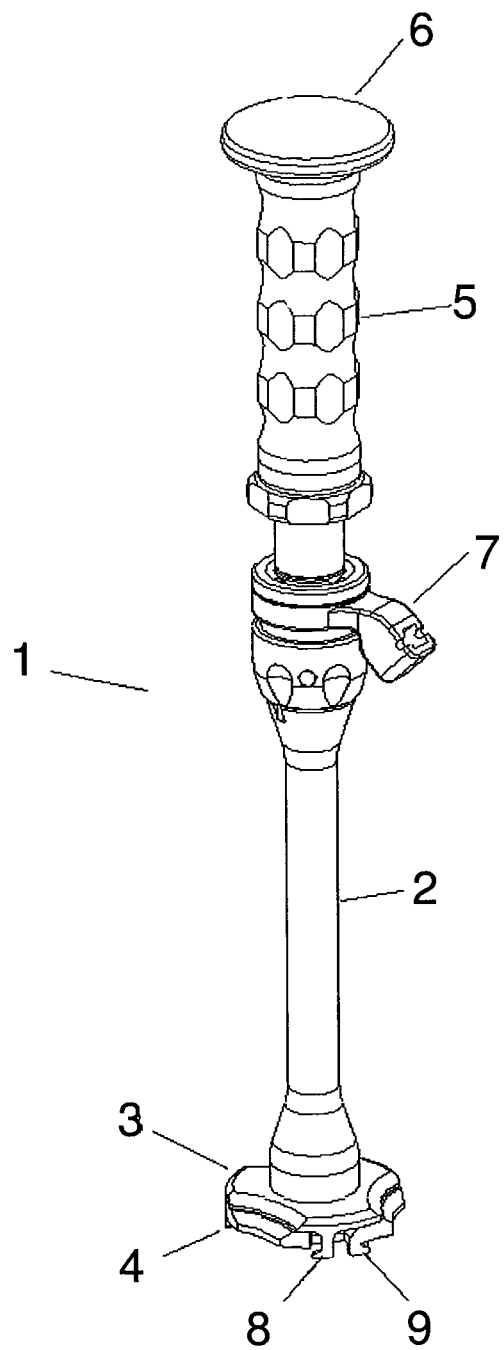
FIG. 1 is a side view of a device according to an embodiment of the present invention.
Figure 2:
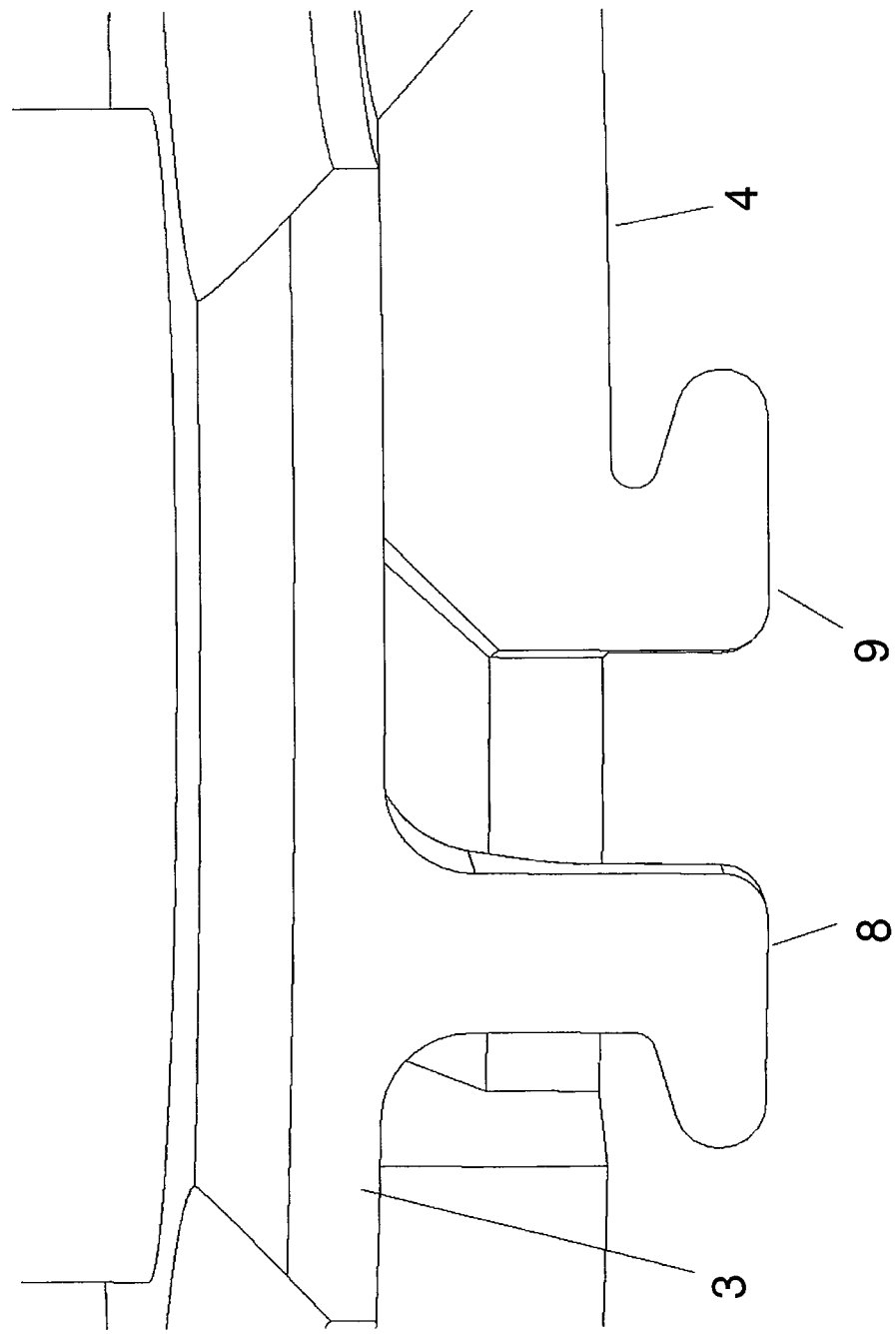
FIG. 2 is an enlarged view of the distal end of the device shown in FIG. 1.

The device 1 shown in FIGS. 1 and 2 comprises a body 2 having a top adapter plate 3 and a bottom adapter plate 4 disposed at the distal end of the body 2. Adapter plates 3 and 4 are connected to protrusions 8 and 9, respectively. In the embodiment shown in FIGS. 1 and 2, adapter plates 3 and 4 have two protrusions 8 and 9. Adapter plates 3 and 4 may have more than two protrusions.

The device of FIG. 1 also comprises an impaction face 6 disposed at the proximal end of handle 5. In use, the surgeon impacts the implant into the acetabulum by applying force to impaction face 6.

The device 1 of FIG. 1 also comprises an attachment point 7 for an alignment guide (not shown). This connection allows a modular design of alignment guide to be attached to the device in order to provide visual assistance with the positioning of the implant.

Figure 3:
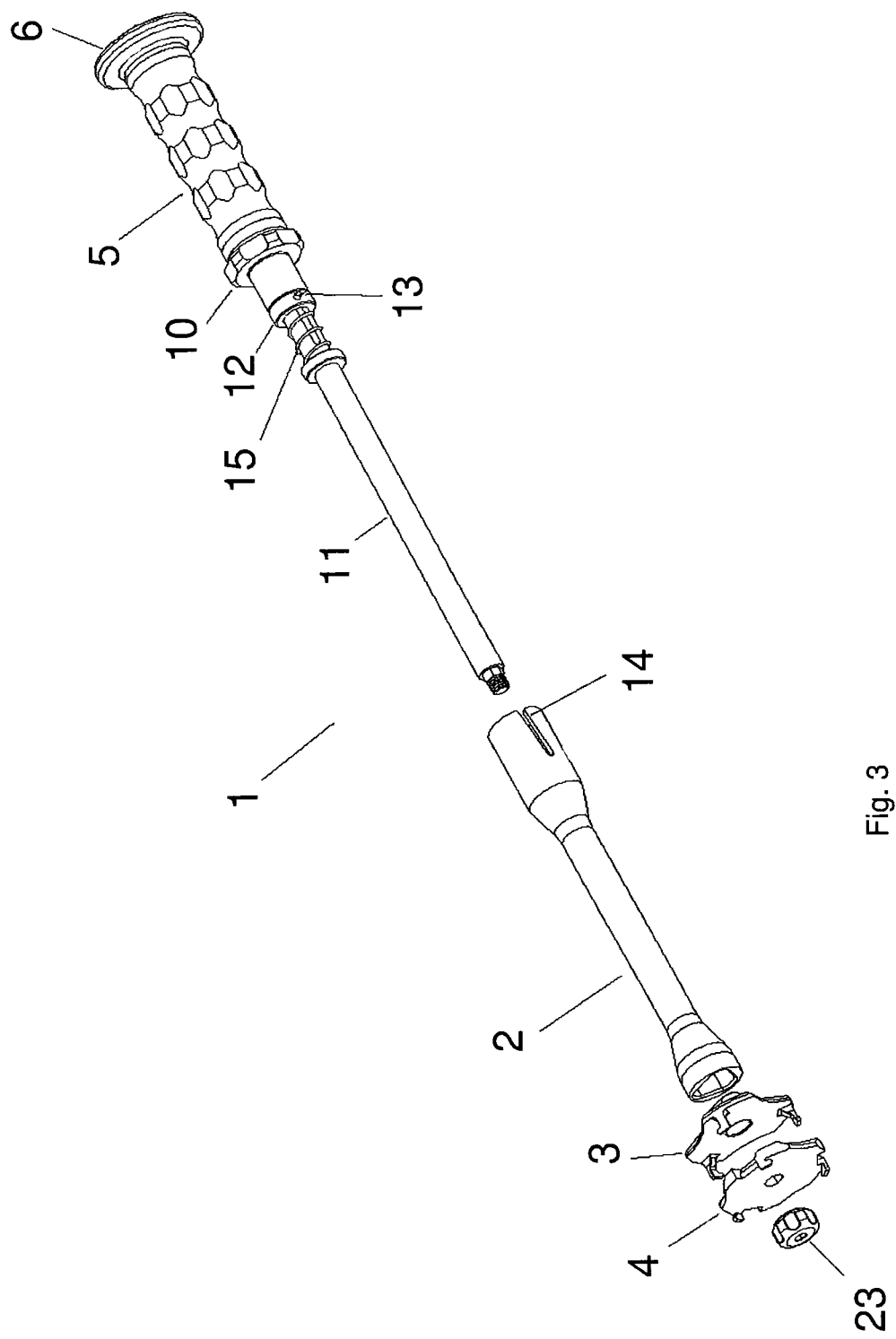
FIG. 3 is an exploded view of the device shown in FIG. 1.

FIG. 3 is an exploded view of the device shown in FIG. 1. For clarity, the attachment point 7 for the alignment guide is not shown. A handle 5 is disposed at the proximal end of the body 2. Body 2 has a conduit for receiving a shaft 11. Positioned distally to the handle 5 is an adjustment screw 10, a ring 12 and a cross pin 13. The ring 12 and cross pin 13 are disposed through a slot in the main shaft. Upon rotation of adjustment screw 10 it advances down the rod 11, and moves the ring 12 and cross pin 13 axially, but they do not rotate.

Body 2 has a partial helix 14 cut-out, which is engaged by cross pin 13. The lateral motion of the cross pin 13 on the helix 14 causes the body 2 to rotate relative to the shaft 11. The adapter plates 3 and 4 are connected to the body 2 and shaft 11, respectively. The design of the mechanism is configured such that rotation of the adjustment screw 10 (relative to the handle 5) causes the adapter plates 3, 4 and protrusions 8, 9 to rotate in opposite directions about the longitudinal axis of body 2.

Positioned distally to the ring 12 is a return spring 15, which allows the mechanism to release when the adjustment screw 10 is retracted. The return spring 15 ensures that the ring 12 is pushed tight against the adjustment screw 10, and so follows any movement of this part.

Figure 4:
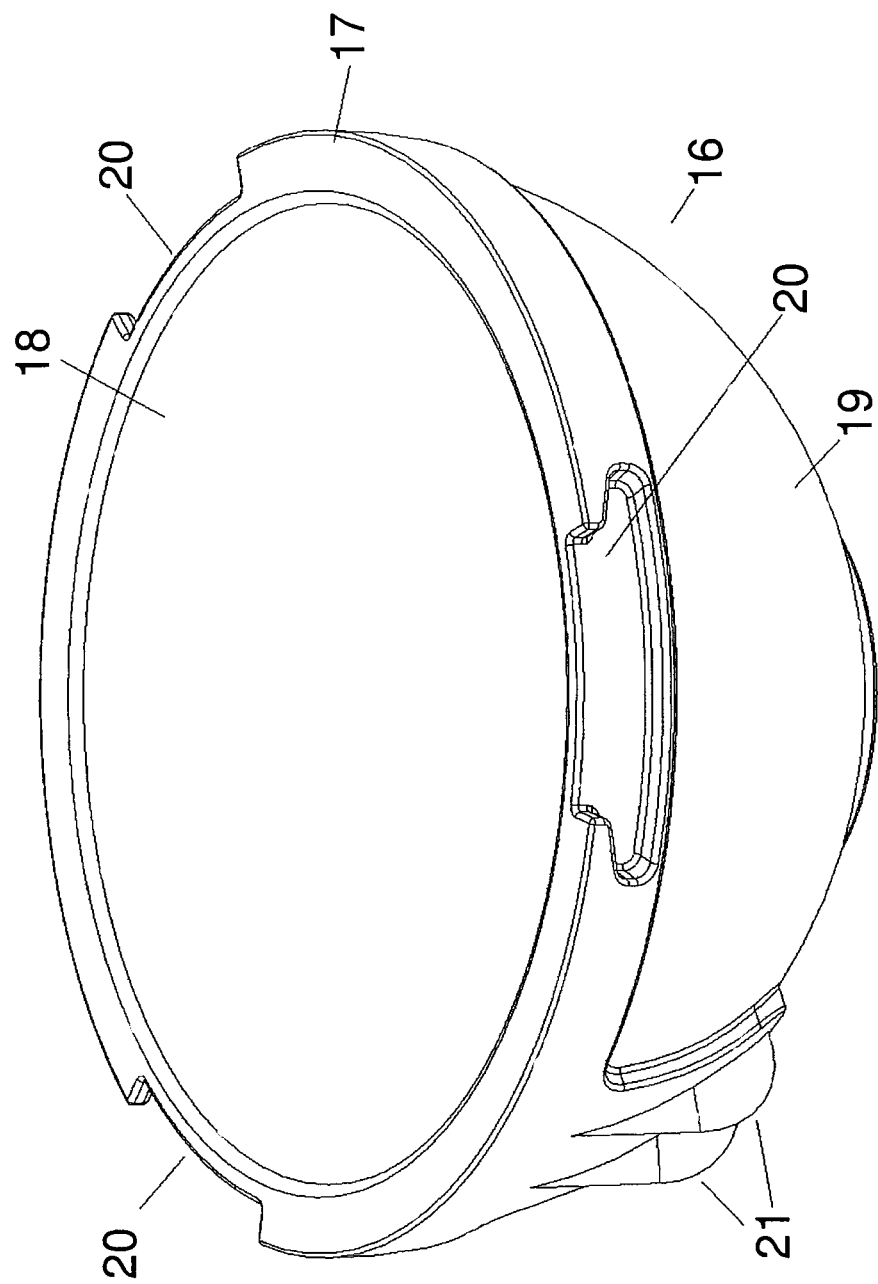
FIG. 4 is a side profile of an implant according to an embodiment of the present invention.

FIG. 4 shows an implant 16 according to an embodiment of the present invention. The implant 16 is an acetabular cup component, having a body 17 comprising an inner bearing surface 18 and an outer surface 19. Three indentations 20 are disposed within the body 17, spaced substantially equidistantly around the periphery of the body 17. Each indentation 20 is shaped so as to receive the two protrusions 8, 9 of device 1, when in use. In the embodiment shown in FIG. 4, each indentation 20 is a chamfered recess having a dovetail shape.

The implant 16 of FIG. 4 also comprises optional anti-rotation fins/blades 21 disposed on the outer surface 19 of body 17. When implanted, fins/blades 21 engage the acetabulum and thereby prevent rotation of the implant 16 within the acetabulum.

Figure 5:
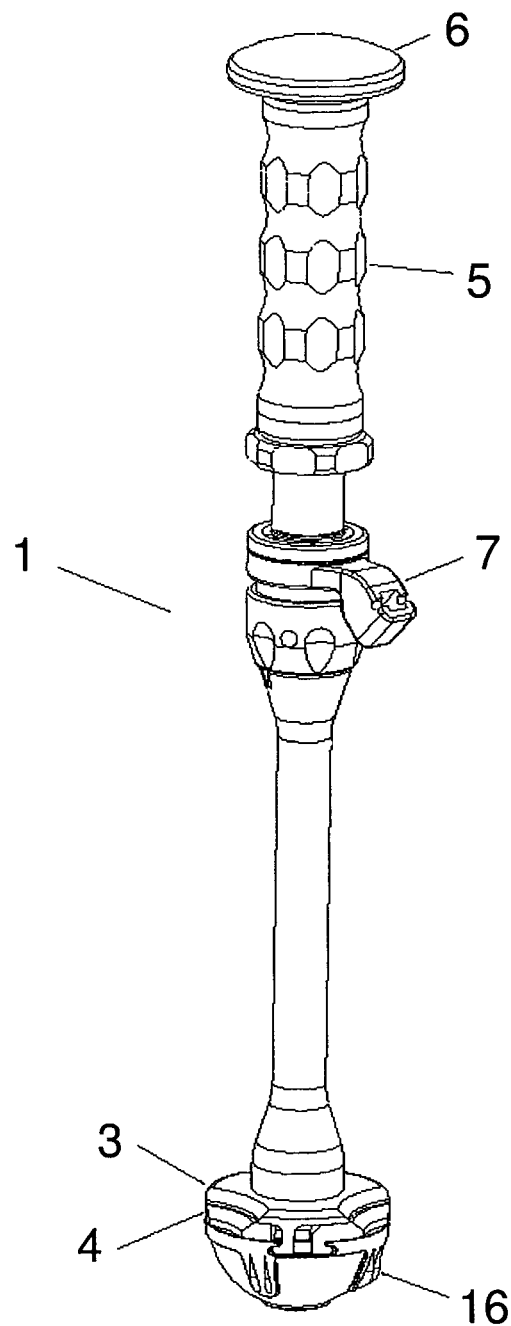
FIG. 5 is a side view of the device of FIG. 1 connected to the implant of FIG. 4.
Figure 6:
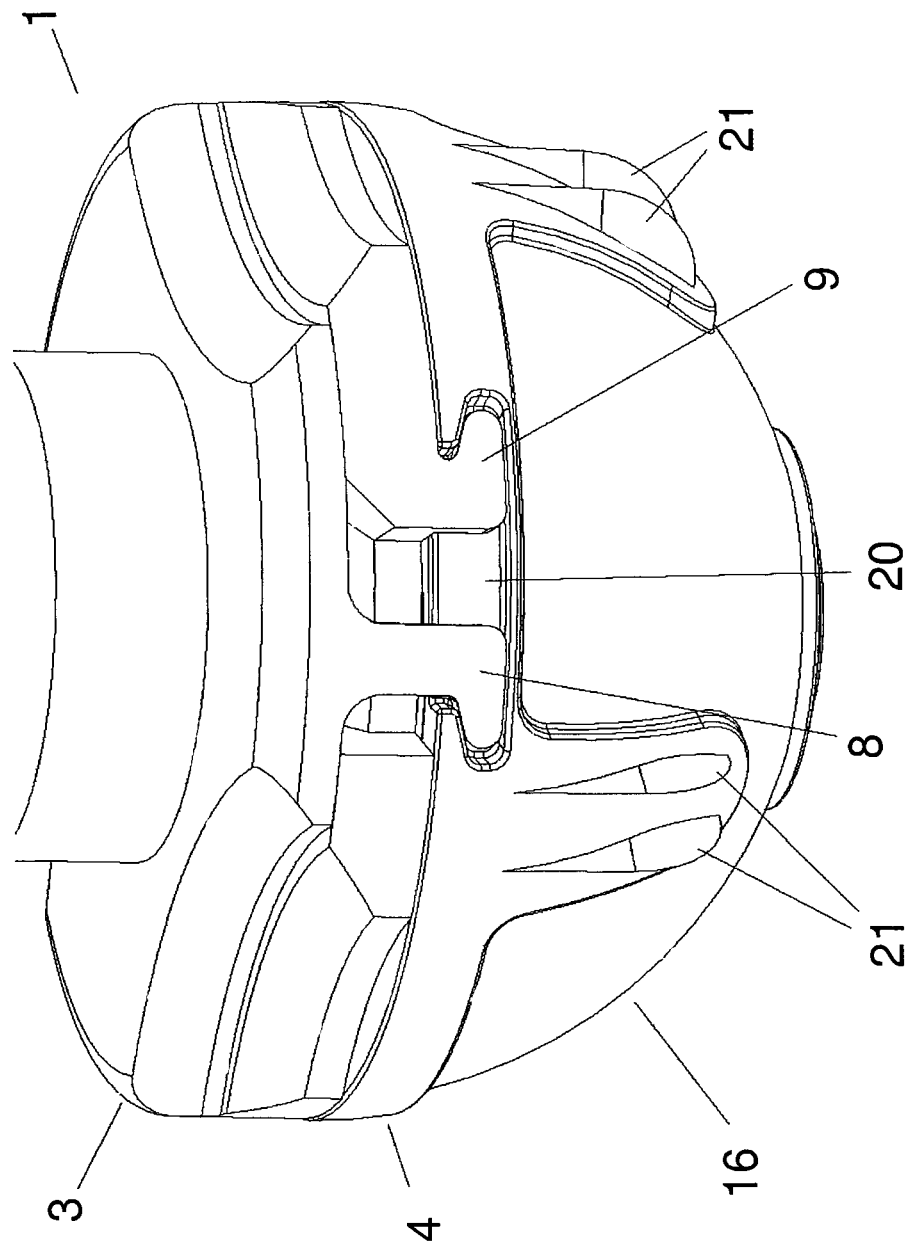
FIG. 6 is an enlarged view of the distal end of the device shown in FIG. 5.

FIGS. 5 and 6 show an implant 16 connected to a device 1. As can be seen more clearly in FIG. 6, indentation 20 of implant 16 is shaped so as to receive protrusions 8, 9 of device 1. The connection between the protrusions 8, 9 and indentation 20 is such that the implant 16 is clamped by the device 1. The connection between the protrusions 8, 9 and indentation 20 is also such that the protrusions 8, 9 do not protrude beyond the inner 18 and outer 19 surfaces of the implant body 17. Accordingly, the implant 16 can be securely connected to the device 1, without compromising the articulating properties or structural strength of the implant 16. The implant 16 can be easily connected to the device 1, both prior to implantation and after implantation (to allow the implant to be removed or repositioned).

Figure 7:
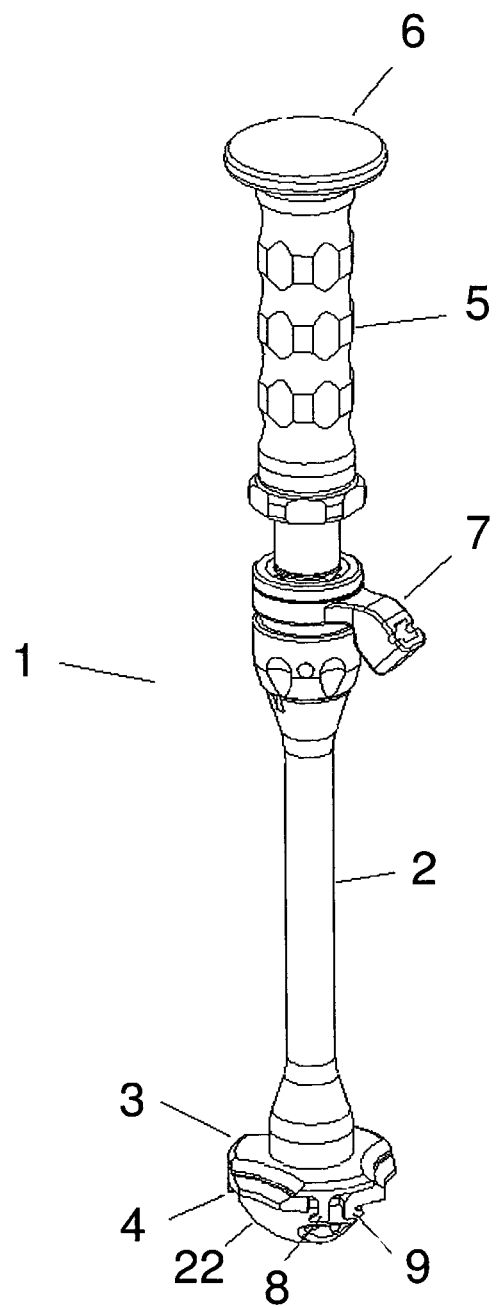
FIG. 7 is a side view of a device according to an embodiment of the present invention.
Figure 8:
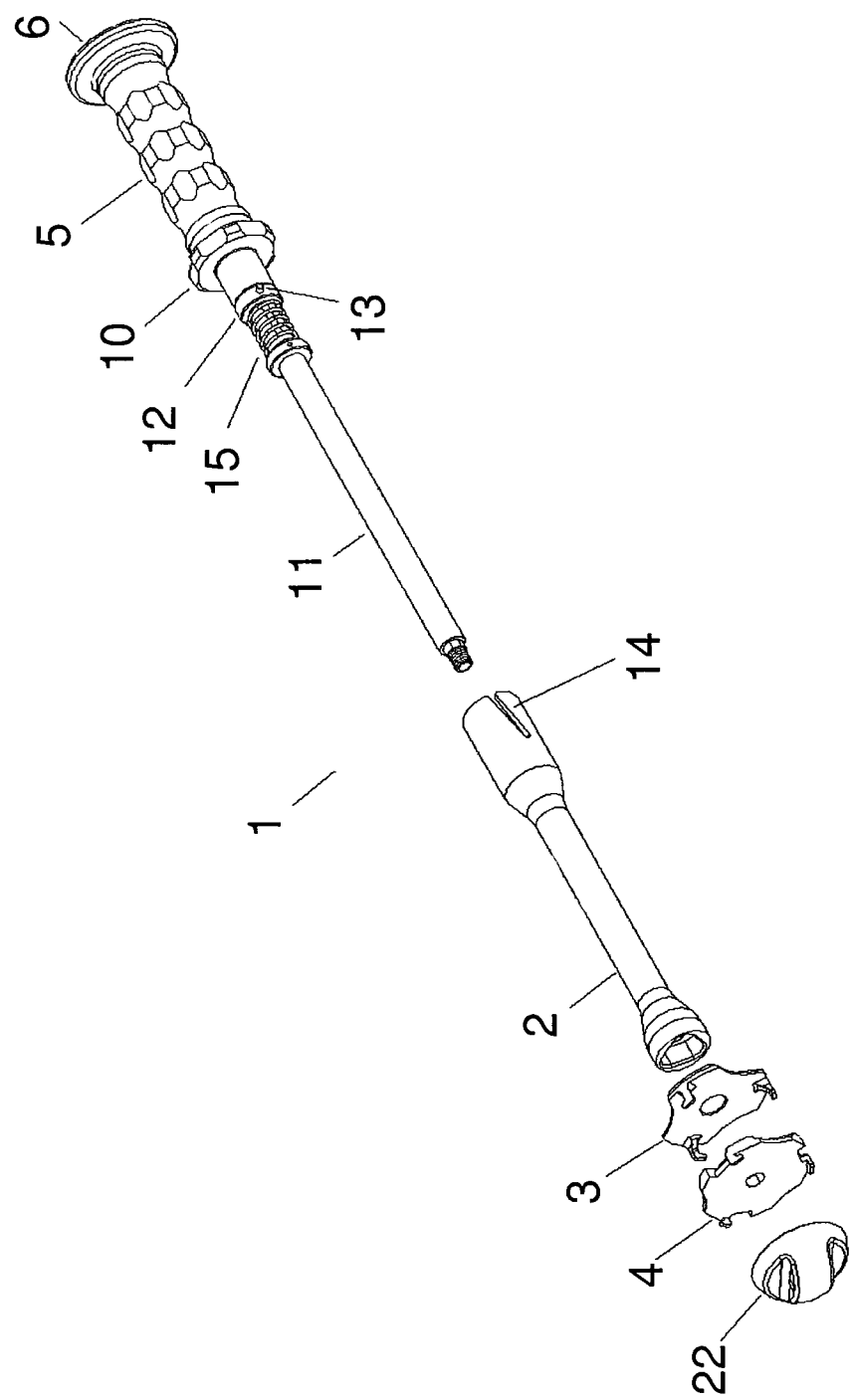
FIG. 8 is an exploded view of the device shown in FIG. 7.

FIGS. 7 and 8 show a device according to another embodiment of the present invention. The screw 22 which is used to hold the entire device together has a hemi-spherical profile, in contrast to the standard screw 23 shown in FIG. 3. The purpose of the hemi-spherical profile is that it acts as a guide when connecting the device 1 to the implant 16, since it helps to locate the protrusions 8, 9 of device 1 to the corresponding indentation 20 on the implant 16. The profile of the screw 22 is designed to be smaller than the inside of the implant 16, in order to ensure that when impacting the implant 16 the force is still transmitted through the top face of the implant body 17.

The invention claimed is:

1. An assembly comprising:
    an implant connection device including at least two protrusions and a mechanism structured to move the protrusions relative to one another in opposite directions between a connected position and a disconnected position; and
    an implant body having an inner surface and an outer surface and at least one indentation disposed within the body between the inner surface and the outer surface, wherein the at least one indentation receives the at least two protrusions of the implant connection device to connect the device to the implant body such that the protrusions do not protrude from the indentation beyond the inner surface of the implant body when the implant connection device is in the connected position.

2. An assembly according to claim 1, wherein the implant body is an acetabular component and wherein the inner surface comprises a hemi-spherical bearing surface.

3. An assembly according to claim 1, wherein the at least one indentation is in the form of a bayonet connector.

4. An assembly according to claim 1, wherein the at least one indentation is shaped so as to receive at least one tapered catch protrusion of the device.

5. An assembly according to claim 1, wherein the protrusions do not protrude from the indentation beyond the outer surface of the implant body.

6. An assembly according to claim 1, wherein the implant connection device is structured to rotate the protrusions relative to one another about a common rotational axis between the connected position and the disconnected position; and
    wherein the protrusions do not protrude from the indentation beyond the inner surface and the outer surface of the implant body when the implant connection device is in the connected position.

7. A method of connecting an implant to a device, comprising:
    providing a device for connecting to an implant, comprising at least two protrusions connectable to at least one indentation in the implant, and a mechanism for moving the protrusions between a connected position and a disconnected position;
    providing an implant comprising an inner surface, an outer surface and at least one indentation positioned between the inner surface and the outer surface; and
    connecting the device to the implant by operating the mechanism so as to move the protrusions relative to one another in opposite directions from the disconnected position to the connected position wherein the protrusions are received within the indentation and do not protrude from the indentation beyond the inner surface of the implant when in the connected position.

8. A method according to claim 7, wherein the protrusions connect to the at least one indentation such that the implant is clamped by the device.

9. A method according to claim 7, wherein the protrusions do not protrude from the indentation beyond the outer surface of the implant when in the connected position.

10. A method according to claim 7, wherein the implant comprises an acetabular component; and
    wherein the inner surface comprises a hemi-spherical bearing surface.

11. A method according to claim 7, wherein the device further comprises a body extending along a longitudinal axis; and
    wherein the operating of the mechanism comprises rotating the body about the longitudinal axis which correspondingly rotates the protrusions relative to one another commonly about the longitudinal axis of the body between the connected position and the disconnected position to connect the device to the implant.

12. A method of connecting an implant to a device, comprising:
- providing a device for connecting to an implant, comprising at least two protrusions connectable to at least one indentation in the implant, and a mechanism for moving the protrusions between a connected position and a disconnected position;
- providing an implant comprising an inner surface, an outer surface and at least one indentation positioned between the inner surface and the outer surface; and
- connecting the device to the implant by operating the mechanism so as to move the protrusions from the disconnected position to the connected position wherein the protrusions are received within the indentation and do not protrude from the indentation beyond the inner surface of the implant when in the connected position; and
- wherein the operating of the mechanism rotates the protrusions relative to one another about a common rotational axis between the disconnected position and the connected position.

13. A method according to claim 12, wherein the operating of the mechanism includes independently rotating the protrusions relative to one another about the common rotational axis between the connected position and the disconnected position.

14. A method according to claim 12, wherein the operating of the mechanism includes rotating the protrusions relative to one another about the common rotational axis and in different directions between the connected position and the disconnected position.

15. A method according to claim 12, wherein the operating of the mechanism includes rotating the protrusions relative to one another about the common rotational axis and in opposite directions between the connected position and the disconnected position.

16. An assembly comprising:
- an implant connection device including at least two protrusions; and
- an implant body having an inner surface and an outer surface and at least one indentation disposed within the implant body between the inner surface and the outer surface, wherein the at least one indentation receives the at least two protrusions of the implant connection device to connect the device to the implant body such that the protrusions do not protrude from the indentation beyond the inner surface of the implant body; and
- wherein the implant connection device includes a mechanism structured to rotate the protrusions relative to one another about a common rotational axis between a connected position and a disconnected position.

17. An assembly according to claim 16, wherein the mechanism is structured to rotate the protrusions independently of each other about the common rotational axis.

18. An assembly according to claim 16, wherein the mechanism is structured to rotate the protrusions in different directions about the common rotational axis.

19. An assembly according to claim 16, wherein the mechanism is structured to rotate the protrusions in opposite directions about the common rotational axis.

20. An assembly according to claim 16, wherein the implant connection device includes a body extending along a longitudinal axis; and
- wherein the mechanism is structured to rotate the body about the longitudinal axis and to correspondingly rotate the protrusions relative to one another about the longitudinal axis between the connected position and the disconnected position.

\* \* \* \* \*